United States Patent
Takahashi et al.

(10) Patent No.: US 8,110,694 B2
(45) Date of Patent: Feb. 7, 2012

(54) METHOD FOR MANUFACTURING DIALKYLALUMINUM MONOHALIDE

(75) Inventors: Hideya Takahashi, Osaka (JP); Tadao Nishida, Osaka (JP); Seijiro Koga, Osaka (JP); Masanori Okutani, Osaka (JP)

(73) Assignee: Nippon Aluminum Alkyls, Ltd. (JP)

( * ) Notice: Subject to any disclaimer, the term of this patent is extended or adjusted under 35 U.S.C. 154(b) by 0 days.

(21) Appl. No.: 12/809,363

(22) PCT Filed: May 7, 2009

(86) PCT No.: PCT/JP2009/058616
§ 371 (c)(1),
(2), (4) Date: Jun. 18, 2010

(87) PCT Pub. No.: WO2010/055704
PCT Pub. Date: May 20, 2010

(65) Prior Publication Data
US 2011/0021800 A1    Jan. 27, 2011

(30) Foreign Application Priority Data
Nov. 12, 2008 (JP) .................................. 2008-289952

(51) Int. Cl.
C07F 5/06 (2006.01)
C07F 3/00 (2006.01)
(52) U.S. Cl. ........ 556/186; 556/118; 556/121; 556/170; 556/187
(58) Field of Classification Search .................. None
See application file for complete search history.

(56) References Cited

U.S. PATENT DOCUMENTS

| | | |
|---|---|---|
| 3,124,604 A | 3/1964 | Huther et al. |
| 3,946,058 A | 3/1976 | Malpass et al. |
| 4,092,342 A | 5/1978 | Mueller |
| 4,670,571 A | 6/1987 | Malpass et al. |
| 4,732,992 A | 3/1988 | Fannin et al. |

FOREIGN PATENT DOCUMENTS

| | | |
|---|---|---|
| CA | 1281733 C | 3/1991 |
| EP | 0272560 A2 | 6/1988 |
| JP | 37-2026 | 2/1959 |
| JP | 63-239288 A | 10/1988 |

OTHER PUBLICATIONS

F.A. Cotton, Basic Inorganic Chemistry, 1994, John Wiley & Sons, Inc., 3rd ed., p. 20.*
International Search Report for Application No. PCT/JP2009/058616 with English translation mailed on Jun. 9, 2009.

* cited by examiner

*Primary Examiner* — Porfirio Nazario Gonzalez
*Assistant Examiner* — James Meadows
(74) *Attorney, Agent, or Firm* — Cantor Colburn LLP

(57) ABSTRACT

A method for manufacturing dialkylaluminum monohalide is provided by which dialkylaluminum monohalide substantially including no zinc component after recovering dialkylzinc from a reaction product obtained by a reaction of zinc halide and trialkylaluminum used as raw materials can be efficiently obtained on an industrial scale at a high yield. According to the method for manufacturing dialkylaluminum monohalide of the present invention, zinc halide is reacted with trialkylaluminum to produce dialkylzinc and dialkylaluminum monohalide, and after the dialkylzinc is separated from a reaction product by distillation, metal aluminum in which a molar ratio is 0.40 or more to zinc component, that is dissolved in the reaction product, and then the mixture is distilled to separate the dialkylaluminum monohalide which substantially includes no zinc component.

3 Claims, 1 Drawing Sheet

METHOD FOR MANUFACTURING DIALKYLALUMINUM MONOHALIDE

CROSS REFERENCE TO RELATED APPLICATIONS

This is a U.S. national stage of application No. PCT/JP2009/058616, filed on 7 May 2009. Priority under 35 U.S.C. §119(a) and 35 U.S.C. §365(b) is claimed from Japanese Application No. 2008-289952, filed 12 Nov. 2008, the disclosure of which is also incorporated herein by reference.

TECHNICAL FIELD

The present invention relates to a method for manufacturing dialkylaluminum monohalide obtained as a coproduct in the making of dialkylzinc used for polymerization catalysts, pharmaceuticals manufacturing, solar cell manufacturing, or the like.

BACKGROUND ART

In recent years, a demand for dialkylzinc has been growing as a catalyst or a reaction agent for polymerization or pharmaceuticals manufacturing, and as a substance for forming zinc oxide that forms a transparent conducting film used for an electrode of solar cells or semiconductor manufacturing devices. As one of the methods for manufacturing dialkylzinc, a reaction of zinc chloride and trialkylaluminium shown in an equation (1) has been known as described in Patent Documents 1 or 2.

$$ZnCl_2 + 2R_3Al \rightarrow R_2Zn + 2R_2AlCl \qquad (1)$$

Dialkylaluminum monohalides, such as dialkylaluminum monochloride obtained as a coproduct of dialkylzinc obtained in the above-mentioned reaction, have functions such as catalytic action for various polymerization reactions, and the usefulness thereof has been observed in various fields.

Dialkylzinc and dialkylaluminum monohalide are manufactured as follows. Usually, first, dialkylzinc which has a lower boiling point is obtained by distillation of a reaction liquid in which dialkylzinc and dialkylaluminum monohalide are produced by a reaction such as the equation (1), then next, dialkylaluminum monohalide which has a higher boiling point is obtained by distillation of the reaction liquid.

While a still pot residue after distillation of dialkylzinc mainly contains dialkylaluminum monohalide, a zinc component still remains. Accordingly, the zinc component is contained in dialkylaluminum monohalide obtained by distilling the pot residue. Various methods for reducing the concentration of zinc component contained in dialkylaluminum monochloride have been reported. For example, Patent Document 3 has disclosed a method for adding trialkylaluminum including alkylaluminum hydride to a pot residue after distilling dialkylzinc, and Patent Document 4 has disclosed a method for adding alkylaluminum sesquichloride to a pot residue after distillation separation of dialkylzinc. However, dialkylaluminum monochloride and trialkylaluminium which have the same number of carbons in alkyl groups have an approximated boiling point. Therefore, separation of these products by distillation is difficult.

Further, Patent Document 5 has reported a method for heating a pot residue at 150 to 240° C. in an inert gas atmosphere after distillation separation of diethylzinc. Patent Document 6 has reported a method for adding aluminum chloride and triethylaluminum, heating the mixture, and subsequently distilling dialkylaluminum monochloride. However, these methods increase steps, additionally, the zinc concentration in diethylaluminum monochloride obtained is 200 mass ppm, 100 mass ppm, or the like, and is not fully reduced.

As mentioned above, a method for manufacturing dialkylaluminum monohalide which substantially includes no zinc component, by which dialkylzinc is separated by distillation from a reaction product obtained by reaction of zinc chloride and trialkylaluminium, and then dialkylaluminum monohalide is separated by distillation from the reaction product at a high yield on an industrial scale, is still desired.

CITATION LIST

Patent Documents

[Patent Document 1] Japanese Patent Publication No. 37-2026
[Patent Document 2] U.S. Pat. No. 3,124,604
[Patent Document 3] U.S. Pat. No. 4,732,992
[Patent Document 4] U.S. Pat. No. 4,670,571
[Patent Document 5] U.S. Pat. No. 3,946,058
[Patent Document 6] U.S. Pat. No. 4,092,342

SUMMARY OF THE INVENTION

Problems to be Solved by the Invention

An object of the present invention is to provide a method for manufacturing dialkylaluminum monohalide, which substantially includes no zinc component, by which dialkylzinc is separated by distillation from a reaction product obtained by a reaction of zinc halide and trialkylaluminium and then dialkylaluminum monohalide is separated by distillation from the reaction product at a high yield on an industrial scale.

Means for Solving the Problems

The present inventors have found that when metallic aluminum is mixed and contacted with a reaction product, which is obtained by a reaction of zinc halide and trialkylaluminium and then separation by distillation of dialkylzinc, a soluble zinc component turns into metal zinc or a zinc component in a solid state, and then, the dialkylaluminum monohalide, which substantially includes no zinc, can be separated by distillation at a high yield. On the basis of this knowledge, the present invention has been completed.

The present invention relates to a method for manufacturing dialkylaluminum monohalide characterized in that zinc halide is reacted with trialkylaluminium to produce dialkylzinc and dialkylaluminum monohalide, and after the dialkylzinc is separated from a reaction product by distillation, metallic aluminum in which a molar ratio is 0.40 or more to zinc component, that is dissolved in the reaction product, is mixed with the reaction product, and then the mixture is distilled to separate the dialkylaluminum monohalide which substantially includes no zinc component.

Advantage of the Invention

According to the method for manufacturing dialkylaluminum monohalide of the present invention, dialkylaluminum monohalide, which substantially includes no zinc component, can be efficiently manufactured on an industrial scale at a high yield by which dialkylzinc is separated by distillation from a reaction product obtained by a reaction of zinc halide and trialkylaluminum and then separation by distillation of the dialkylaluminum monohalide from the reaction product.

DESCRIPTION OF EMBODIMENTS

Figure 1:
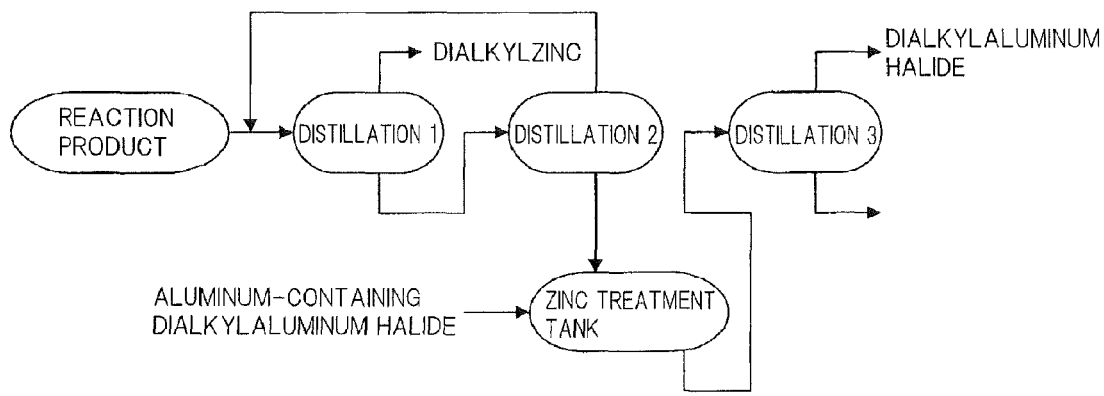
FIG. 1 is a schematic configuration diagram showing an example of a method for manufacturing dialkylaluminum monohalide of the present invention.

A method for manufacturing dialkylaluminum monohalide of the present invention is characterized in that zinc halide is reacted with trialkylaluminium to produce dialkylzinc and dialkylaluminum monohalide, and after the dialkylzinc is separated from a reaction product by distillation, metal aluminum in which a molar ratio is 0.40 or more to zinc component, that is dissolved in the reaction product, is mixed with the reaction product, and then the mixture is distilled to separate the dialkylaluminum monohalide which substantially includes no zinc component.

In the method for manufacturing dialkylaluminum monohalide of the present invention, zinc halide used as a raw material is zinc chloride, zinc iodide, zinc bromide, or the like. The zinc halide need to be sufficiently dried because zinc halide absorbs moisture easily. It is preferable that the moisture content of the zinc halide be 0.5% by mass or less, and more preferably 0.1% by mass or less.

Trialkylaluminum ($R_3Al$) of the other raw material has alkyl groups which may be linear, branched, or cyclic and preferably have carbon number C1 to C6. While three alkyl groups in the trialkylaluminium ($R_3Al$) may be of a different kind, it is preferable that the three alkyl groups be of the same kind.

A reaction of the two above-mentioned raw materials to produce dialkylzinc and dialkylaluminum monohalide can be performed as follows. While the reaction may be performed without a solvent, the reaction may be performed in a dispersion medium. As the dispersed medium, a solvent which does not react with the raw materials and the products and has a boiling point higher than that of the products is suitable for easiness in distillation separation. Hydrocarbons such as liquid paraffin are excellent for use. It is also preferable that the reaction be performed in a dry inert gas atmosphere. This is because when moisture exists within a reactor, the trialkylaluminum reacts with the moisture, thereby reducing the yield of the dialkylzinc.

The reaction of zinc halide and trialkylaluminum is an exothermic reaction. It is preferable that the reaction be performed at temperature in the range of 20 to 100° C., and it is more preferable that the reaction be controlled at the temperature of 30 to 70° C. When a reaction temperature is 20° C. or more, a reaction rate can be prevented from becoming slow. When the reaction temperature is 100° C. or less, formation of a deposited product can be suppressed. A method of controlling the temperature of the reactor can be selected from among ways or their combinations, for example a raw material feeding flow rate, a refrigerant flow rate, or a refrigerant temperature at the time of feeding.

As for a proportion of amounts of the zinc halide and the trialkylaluminum to be used, the trialkylaluminum is preferably 1.6 mol or more and 2.4 mol or less to 1 mol of the zinc halide, and more preferably 1.8 mol or more and 2.2 mol or less.

As preparation of the raw materials in the reactor, it is preferable for easiness of control of the reaction that one of the trialkylaluminum and the zinc halide be put in the reactor, and then the other be gradually fed into it. When the trialkylaluminum is put in the reactor first, these can react without any dispersed medium. By setting appropriate feeding rate of the raw material, heat of reaction per unit time can be prevented from becoming excess to raise the temperature of reaction system. As a result, decomposition loss of the dialkylzinc due to the heat can be suppressed. Moreover, it is preferable that stirring the materials after completing feeding of the raw material be performed for a sufficient period of time until the reaction is completed. Specifically, it preferably takes 1 to 15 hours more preferably 2 to 10 hours to feed the raw material into the reactor where the other raw material has been put. Thereafter, it preferably takes 0.5 to 5 hours more preferably 1 to 3 hours to stir the materials to complete the reaction.

Dialkylzinc and dialkylaluminum monohalide of the target object are recovered from the reaction product by distillation. Here, the reaction product means an entire reaction system after the reaction is completed. Therefore, the reaction product includes the product obtained by the reaction, unreacted raw materials, solvent or the like. It is preferable that distillation column be used for distillation. A distillation method may be any of a batch type or a continuous type. First, the dialkylzinc is distilled from the reaction product. It is preferable that the reaction product be transferred to the distillation column, distillation conditions be selected appropriately, and the dialkylzinc, which substantially includes no aluminum component, namely, an aluminum concentration of 10 ppm by mass or less, be distilled at a yield of 80 to 90%. As the conditions of the dialkylzinc distillation, pressure preferably be reduced in order to suppress thermal decomposition of the dialkylzinc and more preferably 10 Torr or more and 100 Ton or less for separation efficiency. As a form of the distillation column, a packed column having small pressure loss and excellent separation efficiency is preferable and a plate column may be used. The aluminum concentration in the dialkylzinc can be measured by an atomic absorption method.

It is preferable that after the distillation of the dialkylzinc mentioned above, pot residue preferably be distilled again to separate completely the dialkylzinc contained in the reaction product. A distillate of the dialkylzinc here may be added to a reaction product obtained by a reaction of a post-batch.

The reaction product after separation by distillation of the dialkylzinc mentioned above (hereinafter, also referred to as a distillation residue reaction product) is mixed and contacted with metal aluminum, that is hereinafter also referred to as zinc treatment. The zinc treatment is performed for a purpose of turning a zinc component, which is dissolved in the distillation residue reaction product, into a solid-state zinc compound or metal zinc (hereinafter, also referred to as solid-state zinc). Thereby, dialkylaluminum monohalide can be separated by distillation from the distillation residue reaction product.

The distillation residue reaction product includes the solid-state zinc component such as metal zinc, and also zinc compounds dissolved in the distillation residue reaction product (hereinafter, also referred to as soluble zinc). This soluble zinc includes dialkylzinc as a reaction product, dialkylzinc having a larger molecular weight than that of the dialkylzinc as a reaction product, zinc halide as a raw material. It is thought that the dialkylzinc having a larger molecular weight than that of the dialkylzinc as the reaction product is produced by a reaction of trialkylaluminum, which has a larger molecular weight and be contained as impurities in trialkylaluminum used as the raw material, and zinc halide, for example, by a reaction shown in an equation (2).

$$ZnX_2 + R_3Al + R_2R'Al \rightarrow RR'Zn + 2R_2AlX \quad (2)$$

wherein R designates an alkyl group included in the reaction product, R' designates an alkyl group having the carbon number larger than that of R, and X designates a halogen atom.

Among soluble zinc, the zinc halide is in a solid-state at normal temperature and normal pressure, and it is easy to separate the zinc halide from dialkylaluminum halide. However, the dialkylzinc that remains in the distillation residue reaction product has a boiling point close to that of the dialkylaluminum monohalide, a distillate obtained by distillation of the dialkylaluminum monohalide from the distillation residue reaction product is contaminated with dialkylzinc By contacting the dialkylzinc with the metal aluminum, a reaction shown in an equation (3) or the like occurs, for example:

$$3R_2Zn + 2Al \rightarrow 3Zn + 2R_3Al \quad (3)$$

The dialkylzinc is reduced to turn into metal zinc. Thereby, the dialkylaluminum monohalide, which is reduced amount of the dialkylzinc, can be separated by distillation from the distillation residue reaction product.

As a method for mixing and contacting the above-mentioned distillation residue reaction product and the metal aluminum, a method for mixing and contact by stirring the distillation residue reaction product and the metal aluminum in a zinc treatment tank can be applied, specifically, it is preferable to mix and contact in the zinc treatment tank which temperature is in range 10 to 40° C. and equips a liquid circulation apparatus or a stirring apparatus while contact efficiency is increased. The processing time can include 1 to 10 hours in a case of an outdoor tank, for example.

The metal aluminum used for the zinc treatment can be used metal aluminum, which is produced as deposit in the reaction product from dialkylaluminum hydride contained as impurities in the trialkylaluminium as the raw material, in state of suspension as it is or solid separated by filtration. This metal aluminum substantially includes no other element.

Moreover, the metal aluminum, which includes a transition metal, can be used preferably. Specifically, the transition metal included in the metal aluminum can be pointed as example of Ti, V, Fe, Ni, Zr, Pd, or the like. The content thereof is preferably 0.0010 or more and 0.10 or less in an atomic ratio to aluminum, and more preferably 0.0050 or more and 0.10 or less in an atomic ratio to aluminum. When the transition metal is 0.10 or less in the atomic ratio to aluminum, it is possible to suppress deterioration in productive efficiency due to increase in steps such as a separation step or the like.

The content of the transition metal included in the metal aluminum can be specifically measured by an atomic absorption method.

The metal aluminum preferably has a grain shape or a powder shape because a surface area is increased. While a particle diameter of the metal aluminum is particularly not limited, the average particle diameter of 150 μm or less is suitable. Unreacted aluminum which remains in a reaction liquid of trialkylaluminium manufactured by a reaction of hydrogen, aluminum, and olefin can be used suitably for the metal aluminum, because it often contains a proper amount of a transition metal such as Ti, and moreover, also has a particle diameter in the preferable range. Alternatively, metal aluminum which is deposited when aluminum trihalide and trialkylaluminum are reacted to synthesize alkylaluminum halide can be used as the metal aluminum.

An amount of the metal aluminum used in the zinc treatment is preferably 0.40 or more in a mole ratio to the soluble zinc in the distillation residue reaction product. When the metal aluminum is 0.40 or more in the mole ratio, the soluble zinc is fully reduced so that separation removal of the zinc component can be fully performed. The concentration of the soluble zinc in the distillation residue reaction product can be measured by such as an atomic absorption method, for example.

Prior to distillation of the dialkylaluminum monohalide, solid contents such as the metal aluminum, metal zinc, zinc halides, etc. can be also removed from the distillation residue reaction product subjected to the zinc treatment by filtration, etc, that is hereinafter, referred to as a zinc treatment object.

Next, the zinc treatment object is distilled, and the dialkylaluminum monohalide is separated as a distillate. The dialkylaluminum halide with high purity substantially including no zinc component can be obtained as a distillate. It is preferable that the concentration of zinc contained as impurities in the dialkylaluminum halide is not more than 10 ppm.

Hereinafter, an example according to the present invention will be shown with reference to FIG. 1.

Distillation 1 that distills dialkylzinc from a reaction product obtained by a reaction of zinc halide and trialkylaluminium is performed preferably at 0.1 to 10 in a reflux ratio, and more preferably at 1 to 5. The distillation 1 is performed preferably at a distillation pressure of 10 to 100 Torr, and more preferably at 20 to 50 Torr. In order to suppress contamination of the distillate of the dialkylzinc by aluminum, it is preferable that a recovery rate of the dialkylzinc per distillation, namely, a proportion of the dialkylzinc distilled to the dialkylzinc in the reaction product is kept at not more than 95%. Thereby, the dialkylzinc having the aluminum concentration of 10 mass ppm or less can be obtained. A pot liquid temperature rises gradually as distillation progresses and a composition of the pot liquid changes. However, it is preferable that the pot liquid temperature is controlled at 150° C. or less, and more preferably controlled at 120° C. or less. A pot residue of the distillation 1 can be also introduced directly to a zinc treatment tank in which mix contact with metal aluminum is performed. However, in order to fully remove the dialkylzinc from this pot residue, it is preferable that the pot residue is fed to distillation 2. This is because in order to suppress contamination of the dialkylzinc to be distilled by aluminum, the distillation 1 is performed in a state where the dialkylzinc remains in the pot residue.

The distillation 2 that distills and separates most of the dialkylzinc remaining in the pot residue of the distillation 1 can be performed subsequently to the distillation 1. However, the distillation 2 can be also proceeded to every distillation 1 without a break, the pot residues of distillation 1 repeated several times can be once stored in another tank, and then the distillation 2 can be performed all at once. The distillation 2 can be also performed in a reflux ratio of 0 and at approximately the same pressure and pot liquid temperature as those in the distillation 1. However, the distillation 2 can be also accelerated by reducing an operating pressure or raising the pot liquid temperature. A distillate of the distillation 2 can be added to a reaction product of a post batch, and can be used for distillation of the dialkylzinc of the distillation 1. A pot residue of the distillation 2 is fed into a zinc treatment tank in which mixing with metal aluminum is performed.

The zinc treatment is to turn soluble zinc contained in the pot residue of the distillation 2 into solid-state zinc, and can be performed in the zinc treatment tank that accommodates metal aluminum of 0.40 or more in a mole ratio to soluble zinc contained in the pot residue to be processed. The metal aluminum which contains transition metal of 0.0010 or more and 0.10 or less in an atomic ratio to aluminum is also able to be used as above. The treatment can be performed at normal temperature for 1 to 10 hours while stirring, for example.

Solid contents such as the metal aluminum, the metal zinc, the zinc halides, etc. can be also removed from the zinc treatment object subjected to the zinc treatment by filtration or the like.

Next, distillation 3 that distills the zinc treatment object and separates the dialkylaluminum monohalide is performed preferably in a reflux ratio of 0.2 to 5, for example, and more preferably in a reflux ratio of 0.5 to 3. The distillation 3 is performed preferably at a distillation pressure of 10 to 100 Ton, and more preferably at 15 to 50 Torr. Although the pot liquid temperature is different depending on physical properties and operating pressure of an object to be distilled, it is preferable that the distillation 3 be performed at a temperature that does not exceed 250° C. It is preferable that a distillate ratio, i.e., a proportion of a mass of the distillate to a mass of a liquid introduced into the distillation column is 50 to 90% because the dialkylaluminum halide with high purity can be obtained as a distillate. The concentration of the zinc contained as impurities in the dialkylaluminum halide obtained can be less than 10 mass ppm. The pot residue of the distillation 3 can be discarded. Besides that, the pot residue of the distillation 3 can be added into the zinc treatment object to perform the distillation 3.

EXAMPLES

Hereinafter, a method for manufacturing dialkylaluminum halide according to the present invention will be described in detail.

Example 1

Substitution by nitrogen was performed on a 6 m$^3$ carbon steel reactor equipped with a stirrer, a zinc chloride feeding line, a triethylaluminum feeding line, a nitrogen line, and a thermometer. Then, 2300 kg of triethylaluminum was prepared in this reactor at a pressure of 0.01 MPaG. While the stirrer was operated, 1400 kg of zinc chloride was fed into this reactor over 10 hours. Stirring was performed for 2 hours after feeding of zinc chloride was completed. Then, the obtained reaction product was transferred to a five-stage sieve tray type distillation column made of carbon steel and having a pot volume of 6 m$^3$.

The obtained reaction product was distilled. A heat exchanger that heats a pot liquid is an external circulation type, and heats a liquid flowing through a tube side by a heating medium on a side of a body. Under a reduced pressure of 30 Torr, a temperature of the pot liquid of 3600 kg was gradually increased from 30° C. to 90° C., so that the pot liquid was distilled. In the reflux ratio of 3, the distillation 1 and the distillation 2 were performed continuously. The distillate of the distillation 1 was 1100 kg, and the distillate of the distillation 2 was 500 kg. From an analysis of the distillate of the distillation 1, a purity of diethylzinc was 99.9 mass % or more, the aluminum concentration was 10 mass ppm or less, and the zinc concentration was 52.9 mass %. The distillate of the distillation 2 included 70 kg of diethylzinc and 430 kg of diethylaluminum monochloride.

The pot residue of the distillation 2 of 2000 kg was transferred to the zinc treatment tank. The reaction and the same operation as the distillation 1 and the distillation 2 were repeated twice, and the pot residue conducted into the zinc treatment tank was 4000 kg in total. The zinc concentration of soluble zinc included in this liquid was 2.0 mass %. An 800 kg diethylaluminum chloride suspension having 10 mass % of a solid consisting of aluminum 69.4 mass %, titanium 23.6 mass %, and other 7.0 mass % was fed into this liquid, and was stirred for 3 hours. The zinc concentration of soluble zinc included in this treatment liquid was 10 mass ppm or less.

Among the obtained treatment liquid, 4000 kg of the treatment liquid was fed into the distillation column. The distillation 3 was performed under conditions of the pressure of 27 Torr, the pot liquid temperature of 144 to 149° C., and the reflux ratio of 1 so that 3500 kg of a distillate was obtained. The distillate had an aluminum concentration of 22.1 mass %, a chloride concentration of 29.1 mass %, and a zinc concentration of 10 mass ppm or less. Per synthesis, a yield of diethylzinc obtained by distillation and having aluminum of 10 mass ppm or less was 1100 kg, and a yield of diethylaluminum chloride obtained by distillation and having zinc of 10 mass ppm or less was 1750 kg.

Example 2

A reaction was performed in the same manner as in the case of Example 1 to obtain the reaction product. Then, 7100 kg of the pot residue of the distillation 2 was introduced into the zinc treatment tank in which approximately 3600 kg of a solid consisting of aluminum 19.1 mass %, titanium 2.5 mass %, zinc 51.5 mass %, and other 26.9 mass %, and 3600 kg of diethylaluminum chloride existed. The zinc treatment tank was left for three days after introduction of the pot residue. The zinc concentration of soluble zinc was 70 mass ppm.

The distillation 3 was performed on 4000 kg of this liquid in the same manner as in the case of Example 1 to obtain 3500 kg of a distillate. The distillate had an aluminum concentration of 22.2 mass %, a chloride concentration of 29.3 mass %, and a zinc concentration of 10 mass ppm or less.

Example 3

A reaction was performed in the same manner as in the case of Example 1 to obtain the reaction product. Then, 4000 kg of the pot residue of the distillation 2 was introduced into the zinc treatment tank in which approximately 2000 kg of a solid consisting of aluminum 98.5 mass % and zinc 1.5 mass %, and 2000 kg of diethylaluminum chloride existed. The zinc treatment tank was left for three days after introduction of the pot residue. The zinc concentration of soluble zinc was 10 mass ppm or less.

The distillation 3 was performed on 4000 kg of this liquid in the same manner as in the case of Example 1 to obtain 3500 kg of a distillate. The distillate had an aluminum concentration of 22.2 mass %, a chloride concentration of 29.3 mass %, and a zinc concentration of 10 mass ppm or less.

Comparative Example 1

A reaction was performed in the same manner as in the case of Example 1 to obtain the reaction product. Then, 800 kg of the diethylaluminum chloride suspension was changed with 580 kg of a diethylaluminum chloride suspension having a solid of 10 mass % consisting of aluminum 11.4 mass %, titanium 7.8 mass %, zinc 20.7 mass %, and other 60.1 mass %. Except that, the distillation 1, the distillation 2, the zinc treatment, and the distillation 3 were performed in the same manner as in the case of Example 1. The zinc concentration of soluble zinc included in the zinc treatment liquid was 9550 mass ppm. The distillate obtained by the distillation 3 had an aluminum concentration of 22.0 mass %, a chloride concentration of 29.0 mass %, and a zinc concentration of 1000 mass ppm.

Comparative Example 2

The pot residue of the distillation 2 was fed into the distillation 3 without passing through the zinc treatment tank. Except that, the reaction was performed in the same manner as in the case of Example 1 to obtain 3500 kg of a distillate by the distillation 3. The distillate had an aluminum concentration of 21.9 mass %, a chloride concentration of 28.9 mass %, and a zinc concentration of 2200 mass ppm.

TABLE 1

|  |  | Ex. 1 | Ex. 2 | Ex. 3 | Com. Ex. 1 | Com. Ex. 2 |
|---|---|---|---|---|---|---|
| Solid amount for zinc treatment (kg) | | 80 | 3600 | 1155 | 58 | 0 |
| Solid composition for zinc treatment (mass %) | Al | 69.4 | 19.1 | 98.5 | 11.4 | — |
| | Ti | 23.6 | 2.5 | 0 | 7.8 | — |
| | Zn | 0 | 51.5 | 1.5 | 20.7 | — |
| | Others | 7.0 | 26.9 | 0 | 60.1 | — |
| Aluminum amount in solid for zinc treatment (kg) | | 56 | 690 | 1138 | 6.6 | — |
| Soluble zinc amount (kg) | | 80 | 142 | 80 | 80 | 80 |
| Al/soluble zinc (mole ratio) | | 1.7 | 11.7 | 34.5 | 0.38 | 0 |
| Ti/Al (Atomic ratio × $10^{-3}$) | | 16 | 6.2 | 0 | 32 | — |
| Zinc concentration in prepared liquid of distillation 3 (mass ppm) | | Not more than 10 | 70 | Not more than 10 | 9550 | 20000 |
| DEAC(*) yield (kg/one synthesis) | | 1750 | 1750 | 1750 | 1750 | 1750 |
| Zinc concentration in DEAC (mass ppm) | | Not more than 10 | Not more than 10 | Not more than 10 | 1000 | 2200 |

INDUSTRIAL APPLICATION FIELD

A method for manufacturing dialkylaluminum monohalide according to the present invention is applied to industrial manufacturing. Products having higher purity can be manufactured efficiently, and products suitable for polymerization catalysts, pharmaceuticals manufacturing, solar cell manufacturing, etc. can be obtained.

The invention claimed is:

1. A method for manufacturing dialkylaluminum monohalide comprising:
   reacting a zinc halide with trialkylaluminium to produce a reaction mixture comprising dialkylzinc and dialkylaluminum monohalide;
   distilling a portion of the dialkylzinc from the reaction mixture;
   adding metal aluminum to the reaction mixture, wherein the metal aluminum is at a molar ratio of 0.40 or more to zinc component that is dissolved in the reaction mixture; and then
   distilling the dialkylaluminum monohalide from the reaction mixture, wherein the dialkylaluminum monohalide distillate includes zinc as an impurity of not more than 10 ppm.

2. The method for manufacturing dialkylaluminum monohalide according to claim 1, wherein the aluminum metal includes a transition metal in which an atomic ratio of the transition metal to the aluminum metal is 0.0010 or more and 0.10 or less.

3. The method for manufacturing dialkylaluminum monohalide according to claim 1, wherein the trialkylaluminum is triethylaluminum.

* * * * *